US011383233B1

(12) United States Patent
Wu et al.

(10) Patent No.: US 11,383,233 B1
(45) Date of Patent: Jul. 12, 2022

(54) DIAGNOSIS METHOD AND DIAGNOSIS DEVICE OF ECOTOXICITY OF SOLID WASTE SOIL IN PESTICIDE PRODUCTION SITE

(71) Applicant: Nanjing Institute of Environmental Sciences, MEE, Nanjing (CN)

(72) Inventors: Shengmin Wu, Nanjing (CN); Feng Tian, Nanjing (CN); Yang Gong, Nanjing (CN); Zhenqian Zhao, Nanjing (CN); Jing Tian, Nanjing (CN)

(73) Assignee: Nanjing Institute of Environmental Sciences, MEE, Nanjing (CN)

( * ) Notice: Subject to any disclaimer, the term of this patent is extended or adjusted under 35 U.S.C. 154(b) by 0 days.

(21) Appl. No.: 17/576,915

(22) Filed: Jan. 15, 2022

(30) Foreign Application Priority Data

Feb. 3, 2021 (CN) ........................ 202110152546.9

(51) Int. Cl.
*G01N 33/24* (2006.01)
*B01L 3/00* (2006.01)
(Continued)

(52) U.S. Cl.
CPC .......... *B01L 3/502* (2013.01); *A61K 49/0004* (2013.01); *G01N 33/24* (2013.01); *G01N 33/5014* (2013.01); *G01N 33/5085* (2013.01); *G01N 33/5088* (2013.01); *B01L 2200/026* (2013.01); *B01L 2200/143* (2013.01);
(Continued)

(58) Field of Classification Search
CPC ............... B01L 3/502; B01L 2200/026; B01L 2200/143; B01L 2300/0663; B01L 2300/0681; B01L 2300/168; B01L 2300/1805; B01L 2400/048; A61K 49/0004; G01N 33/24; G01N 33/5014; G01N 33/5085; G01N 33/5088
See application file for complete search history.

(56) References Cited

FOREIGN PATENT DOCUMENTS

CN 102495197 A 6/2012
CN 102590478 A 7/2012
(Continued)

OTHER PUBLICATIONS

First Examination Letter of Opinion, issued in Chinese Application 202110152546.9 (priority application) by Chinese State Intellectual Property Office, dated Sep. 1, 2021.
(Continued)

*Primary Examiner* — Dennis White
(74) *Attorney, Agent, or Firm* — Zhu Lehnhoff LLP

(57) ABSTRACT

The disclosure relates to a diagnosis method and diagnosis device of ecotoxicity of solid waste soil in a pesticide production site. The diagnosis method is as follows: performing multi-point distributed collection on solid waste soil of a to-be-diagnosed pesticide production site, and subsequently pretreating the connected soil sample; synchronously performing a first toxicity test, a second toxicity test and a third toxicity test on the pretreated solid waste soil by using the diagnosis device. The diagnosis device comprises a first test device, a second test device and a third test device. The method of the disclosure is used for synchronous diagnosis of ecotoxicity by utilizing multiple diagnosis methods, and therefore is high in diagnosis efficiency and high in accuracy rate.

7 Claims, 5 Drawing Sheets

(51) Int. Cl.
*G01N 33/50* (2006.01)
*A61K 49/00* (2006.01)

(52) U.S. Cl.
CPC .................. *B01L 2300/0663* (2013.01); *B01L 2300/0681* (2013.01); *B01L 2300/168* (2013.01); *B01L 2300/1805* (2013.01); *B01L 2400/0487* (2013.01)

(56) References Cited

FOREIGN PATENT DOCUMENTS

| | | | | |
|---|---|---|---|---|
| CN | 103056159 | A | | 4/2013 |
| CN | 104198678 | A | | 12/2014 |
| CN | 105181936 | A | | 12/2015 |
| CN | 105223334 | A | * | 1/2016 |
| CN | 105223334 | A | | 1/2016 |
| CN | 105303015 | A | | 2/2016 |
| CN | 109580913 | A | | 4/2019 |
| CN | 208780701 | U | | 4/2019 |
| CN | 109709304 | A | | 5/2019 |
| CN | 111443192 | A | | 7/2020 |
| CN | 112946242 | A | | 6/2021 |

OTHER PUBLICATIONS

Notice of Grant, issued in Chinese Application 202110152546.9 (priority application) by Chinese State Intellectual Property Office, dated Oct. 11, 2021.

Search Report, issued in Chinese Application 202110152546.9 (priority application) by Chinese State Intellectual Property Office, dated Aug. 26, 2021.

Liping Zheng, "Study on the diagnosis and determination method of soil biotoxicity in the soil of chlordane and tricycline pollution sites," Nanjing Agricultural University, Master's Thesis, Dec. 2010.

Xia Xu et al., "Screening of Acute Toxicity and Genetic Toxicity of Soil Leachates from Abandoned Pesticide Factory Contaminated Site," Asian Journal of Ecotoxicology, 2017, 12(6): 223-232.

Yan Cheng, "Application of Earthworm Acute Toxicity Test and Plant Growth Inhibition Test on Pesticide Production Solid Wastes' Inherent Eco-toxicity Test," Pesticide Science and Administration, Article No. 1002-5480, 2015, 36 (4).

Search Report, issued by Beijing Zhanqiao Intellectual Property Agency, dated Jul. 21, 2021.

* cited by examiner

DIAGNOSIS METHOD AND DIAGNOSIS DEVICE OF ECOTOXICITY OF SOLID WASTE SOIL IN PESTICIDE PRODUCTION SITE

The present application claims the priority of Chinese Patent Application No. CN202110152546.9, filed Feb. 3, 2021, the disclosure of which is hereby incorporated by reference in its entirety.

TECHNICAL FIELD

The disclosure relates to the technical field of soil ecological environment, particularly to a diagnosis method and diagnosis device of ecotoxicity of solid waste soil in a pesticide production site.

BACKGROUND

With the development of industrialization, parts of pesticide production enterprises use simple equipment and backward processes, and have no relevant environmental protection measures during the production, so surrounding places can be seriously contaminated by long-term pesticide production.

Especially, in pesticide production sites, pesticides are neither easy to evaporate, volatilize, nor decomposed by soil microorganisms, so they are pollutants remained in soil for long time. Due to the lack of effective management and repairing, such the pollutants have seriously harmed natural environments; furthermore, it is also very easy for such the pollutants in the soil to be eluted into the groundwater due to inducements such as rain, so that the groundwater is contaminated, or migrated with direct surface runoff to result in pollution of the surface water.

Therefore, there is an urgent to effectively manage and repair contaminated soil in pesticide production sites, and diagnostic technologies for contaminated soil can provide an important basis for management and repairing; however, how to rapidly and effectively diagnose the contaminated soil in pesticide production sites has become a primary issue to be solved.

SUMMARY

In order to solve the above technical problem, the disclosure provides a diagnosis method and diagnosis device of ecotoxicity of solid waste soil in a pesticide production site. The method of the disclosure can effectively and rapidly diagnose the contaminated soil in the site; the device of the disclosure is simple in practical operation, and has relatively high diagnosis efficiency when in actual use.

The technical solution of the disclosure is as follows: provided is a diagnosis method of ecotoxicity of solid waste soil in a pesticide production site, comprising:

Step 1: Collection of Solid Waste Soil in a Site performing multi-point distributed collection on to-be-diagnosed solid waste soil in a pesticide production site in combination with a layout principle of survey spots in the pesticide production site to obtain a soil sample;

Step 2: Pretreatment of Solid Waste Soil removing the impurities in the collected soil sample, smashing, and screening via a 5-10 mm sieve to obtain pretreated solid waste soil; and Step 3: Diagnosis of Ecotoxicity performing a first toxicity test, a second toxicity test and a third toxicity test on the pretreated solid waste soil by using a diagnosis device, wherein the first toxicity test is an earthworm toxicity test and a plant germination toxicity test, the second toxicity test is a fish feeding toxicity test, and the third toxicity test is a plant root extension toxicity test.

The disclosure also provides a diagnosis device special for the above diagnosis method, comprising:

a first test device for a first toxicity test, wherein *Eisenia foetidas* which are subjected to intestinal cleaning treatment for 3-5 h in a humid environment are placed inside the first test chambers of the first test device;

a second test device for a second toxicity test, wherein zebrafish which are subjected to fasting for 36-48 h in a humid environment are placed inside the second test chambers of the second test device;

and a third test device for a third toxicity test, wherein hydroponic vegetables are placed inside the third test chambers of the third test device.

As one aspect of the disclosure, the first test device, the second test device and the third test device are successively connected;

the first test device comprises:

5-8 first test chambers with the same structure and arranged inside the cavity body of the first test device at equal intervals in parallel, wherein the first test chamber comprises a first housing made of a transparent acrylic plate and 3-5 embedded clapboards which are successively clamped with the first housing via an abutment component from top to bottom, wherein embedded holes for embedding seeds and perforated grooves for allowing earthworms to pass through are staggered on the embedded clapboards at equal intervals, first monitoring devices uniformly arranged on one side wall of each of the first test chambers, wherein the number of the first monitoring devices is plural, and a first connection device for connecting the first test chambers and the second test device, wherein the first connection device comprises liquid supply components which are in one-to-one correspondence with 5-8 first test chambers and used for supplying liquid to the first test chambers, a liquid infiltration component arranged at the lower ends of the first test chambers, and a first connection component in which one end is connected with the liquid infiltration component and the other end is connected with the second test device, and the first connection component comprises a pipeline and a pump;

the second test device comprises:

5-8 second test chambers with the same structure and arranged in parallel, wherein the 5-8 second test chambers are respectively connected with branch pipes on the pipeline of the first connection component, and a second monitoring device erected above the second test chambers and an auxiliary device;

the third test device comprises:

5-8 third test chambers with the same structure and arranged in parallel, and a second connection component correspondingly connected with the 5-8 third test chambers and the 5-8 second test chambers one by one, wherein the second connection component comprises a pipeline and a pump.

As one aspect of the disclosure, the abutment component comprises:

an abutment sleeve arranged on the clamping hole of the first housing, wherein a slidable transmission sleeve is arranged in the abutment sleeve, and the transmission sleeve is provided with a guide block clamped with an arc groove arranged on the inner side wall of the abutment sleeve, and an abutment rod arranged on the embedded clapboard, wherein one side of the abutment rod close to the abutment sleeve is provided with a vertical plate-shaped first clamp head, the first clamp head is connected with the abutment rod through a horizontally arranged transverse plate-shaped second clamp head, and the second clamp head is rotatably connected with the first clamp head through a torsion spring, and the second clamping head is fixedly connected with the abutment rod;

the side surface of the abutment sleeve is provided with a linear strip-shaped hole corresponding to the horizontally arranged second clamp head, the abutment sleeves on the upper and lower sides of the strip-shaped hole are respectively provided with a clamp seat, and the clamp seat is clamped with a clamp slot matched with the first clamp head, the transmission sleeve is provided with through holes matched with the first clamp head and the second clamp head, and the lengths of the through holes, the length of the first clamp head and the length of the second clamp head are equal, the inner side surfaces of the transmission sleeve and the abutment sleeve are provided with magnetic sheets whose magnetic poles are mutually repellent.

Through the arrangement of the above abutment component, the quick plug-in installation of the embedded clapboard and the first housing can be realized, so as to improve the installation efficiency of the first test chambers, and the quantity of the first test chambers is rapidly adjusted according to demand on the practical diagnosis method.

As one aspect of the disclosure, the liquid supply component comprises a storage box for storing deionized water, a spraying member arranged on the inner wall of the first housing as well as a pipeline and a pump which are used for connecting the storage box with the spraying member and a soil humidity sensor is arranged on the inner wall of the first housing; by using the liquid supply component, the maximum water content of the soil inside the first test chamber is always maintained to 60%, or the deionized water can be continuously injected into the buffer cavities by utilizing the liquid supply component, the pollutants carried in the pretreated solid soil in the first toxicity test are imported into the subsequent second test chambers through the pipeline and pump connected with the buffer cavities;

the liquid infiltration component comprises 5-8 buffer cavities correspondingly installed at the bottom of the first housing one by one and communicated with the first test chambers, and an intercepting filter screen arranged at a communication position between the buffer cavity and the first housing, the buffer cavities are connected with a water tank through the pipeline and the pump, and the water tank is arranged at a gap between the first test device and the second test device; the use of the intercepting filter screen can effectively avoid that the pretreated solid waste soil in the first test chambers flow into the buffer cavities, arrangement of buffer cavities can effectively prevent the block of the pipeline of the first connection component, and when in actual use, the first connection component is used to connect the position of the buffer cavity close to the upper part.

As one aspect of the disclosure, the auxiliary device includes an air pump for supplying oxygen to the second test chambers and a heating device for helping to heat the second test chambers, the air pump is connected with an air pipe arranged in each second test chamber, and the heating device is connected with a heating plate arranged in each second test chamber; by utilizing the air pump and the heating device, a more suitable environment can be provided for cultivation of zebrafish, and the death of zebrafish caused by oxygen deficit, low temperature, high temperature and the like can be effectively avoided, thereby reducing the influence of these interference factors on accuracy rate of actual diagnosis.

The disclosure has the beneficial effects:

(1) The diagnosis method of the disclosure is simple in practical operation, is capable of collecting the to-be-diagnosed pesticide production site containing the solid waste soil by means of multi-point distributed collection, can perform synchronous diagnosis by using multiple diagnosis methods, and therefore has high diagnosis efficiency and better accuracy rate.

(2) The overall structure of the diagnostic device of the disclosure is reasonable in design, and the to-be-diagnosed soil sample can undergo a variety of different diagnosis methods through cooperative use of the first test device, the second test device and the third test device; by using the diagnosis device, multiple and detailed experiments can be conducted within effective experimental time to improve the efficiency and accuracy of soil ecotoxicity diagnosis; the diagnosis device is suitable for large-scale promotion.

In which, 1-first test device, 11-first test chamber, 111-first housing, 112 embedded clapboard, 1121-embedded hole, 1122-perforated groove, 12-first monitoring device, 13-first connection device, 131-first connection component, 132-storage box, 133-spraying member, 134-buffer cavity, 135-intercepting filter screen and 136-water tank,

2-second test device, 21-second test chamber, 22-second monitoring device, 23-auxiliary device, 231-air pipe, 232-heating plate,

3-third test device, 31-third test chamber, 32-second connection component,

4-abutment component, 41-abutment sleeve, 411-arc groove, 412-strip-shaped hole, 413-clamp seat, 42-abutment rod, 43-transmission sleeve, 431-guide block, 432-through hole, 44-first clamp head, 441-clamp slot, 45-second clamp head, and 46-torsion spring.

DETAILED DESCRIPTION OF THE EMBODIMENTS

The disclosure will be further described in detail in combination with specific embodiments to better embody the advantages of the disclosure.

Example 1

A diagnosis method of ecotoxicity of solid waste soil of a pesticide production site includes the following steps:

step 1: collection of solid waste soil in a site

Multi-point distributed collection was performed on to-be-to diagnosed solid waste soil in a pesticide production site in combination with a layout principle of survey spots in the pesticide production site to obtain a soil sample;

step 2: pretreatment of solid waste soil

The impurities in the collected soil sample was removed, and the soil sample without the impurities were smashed and screened via a 5 mm sieve to obtain pretreated solid waste soil; and step 3: diagnosis of ecotoxicity A first toxicity test, a second toxicity test and a third toxicity test were performed on the pretreated solid waste soil by using a diagnosis device the first toxicity test was an earthworm toxicity test and a plant germination toxicity test, the second toxicity test was a fish feeding toxicity test, and the third toxicity test was a plant root extension toxicity test.

Example 2

Figure 1:
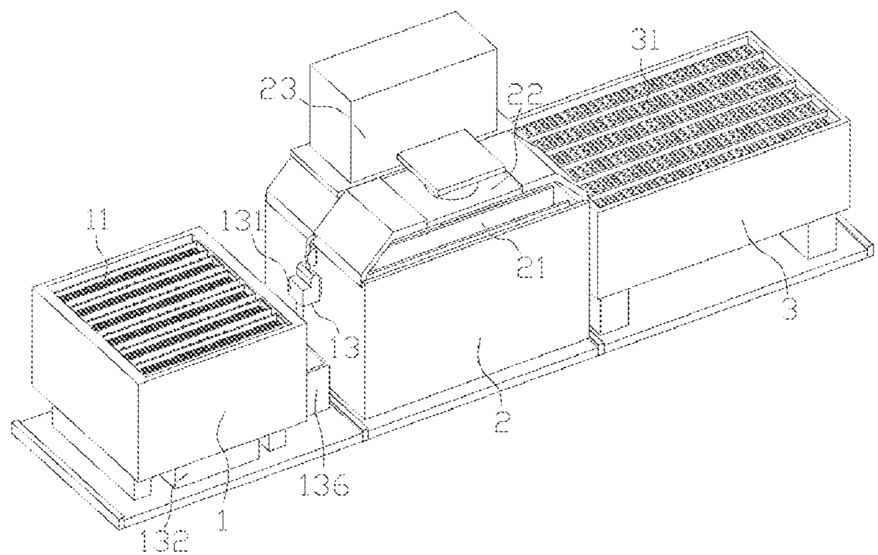
FIG. 1 is a diagram of an overall structure of a diagnostic device according to the disclosure.
Figure 2:
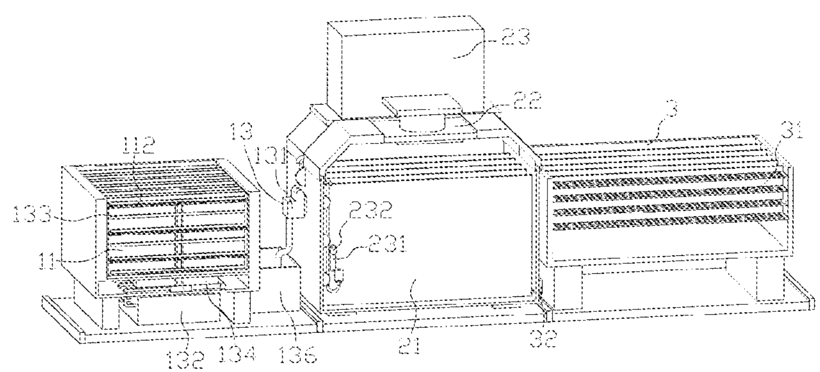
FIG. 2 is a diagram of a partial sectional structure of a diagnostic device according to the disclosure.

A diagnostic device special for the diagnostic method in example 1 was recorded in this example, as shown in FIGS. 1 and 2. The above diagnostic device for diagnosing the ecotoxicity of solid waste soil in a pesticide production site in cooperation with the diagnostic method includes: a first test device 1 for a first toxicity test, wherein *Eisenia foetidas* which are subjected to intestinal cleaning treatment for 3 h in a humid environment are placed inside the first test chambers 11 of the first test device 1; a second test device for a second toxicity test, wherein zebrafish which are subjected to fasting for 36 h in a humid environment are placed inside the second test chambers 21 of the second test device 2; and a third test device 3 for a third toxicity test, wherein hydroponic vegetables are placed inside the third test chambers 31 of the third test device 3.

Figure 3:
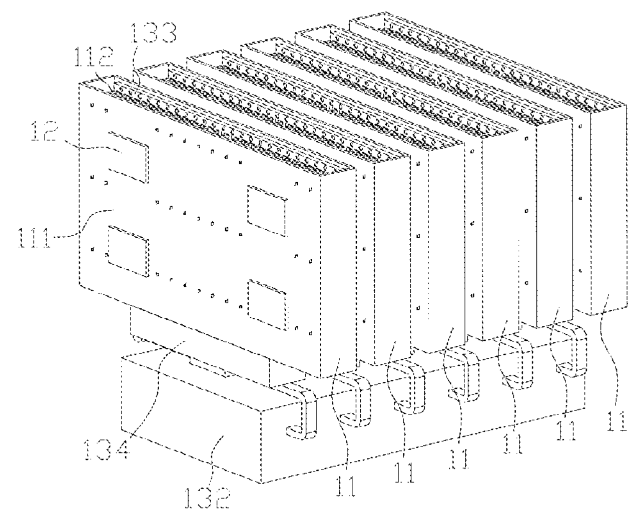
FIG. 3 is a structural diagram of a first test device according to the disclosure.
Figure 5:
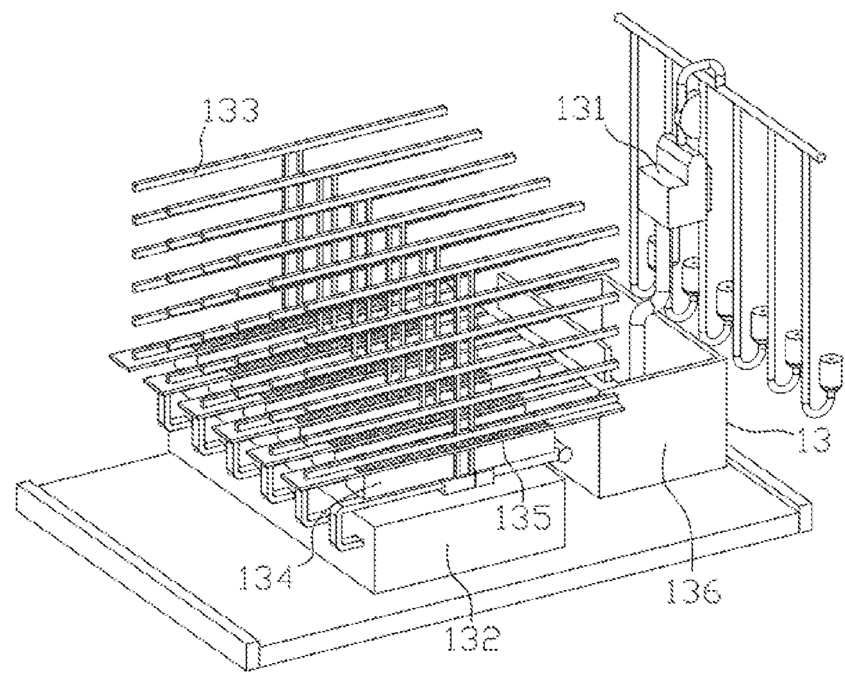
FIG. 5 is a structural diagram of a first connection device according to the disclosure.
Figure 6:
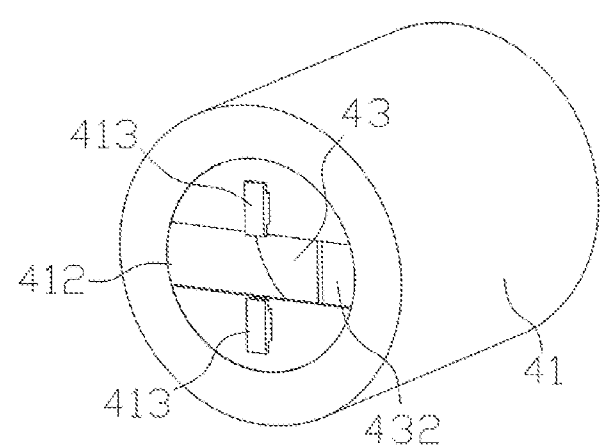
FIG. 6 is a structural diagram of an abutment sleeve of an abutment component according to the disclosure.

As shown in FIG. 1, the first test device 1, the second test device 2 and the third test device 3 are successively connected;

the first test device 1 includes:

as shown in FIG. 3, 6 first test chambers 11 with the same structure and arranged inside the cavity body of the first test device 1 at equal intervals in parallel, wherein the first test chamber 11 includes a first housing 111 made of a transparent acrylic plate and 3 embedded clapboards 112 which are successively clamped with the first housing 111 via an abutment component 4 from top to bottom, wherein embedded holes 1121 for embedding seeds and perforated grooves 1122 for allowing earthworms to pass through are staggered on the embedded clapboards 112 at equal intervals, as shown in FIG. 3, first monitoring devices 12 uniformly arranged on one side wall of each of the first test chambers 11, wherein the number of the first monitoring devices 12 is 4, as shown in FIG. 5, a first connection device 13 for connecting the first test chambers 11 and the second test device 2, wherein the first connection device 13 includes liquid supply components which are in one-to-one correspondence with 6 first test chambers 11 and used for supplying liquid to the first test chambers 11, a liquid infiltration component arranged at the lower ends of the first test chambers 11, and a first connection component 131 in which one end is connected with the liquid infiltration component and the other end is connected with the second test device 2, and the first connection component 131 includes a pipeline and a pump, as shown in FIG. 5, the liquid supply component includes a storage box 132 for storing deionized water, a spraying member 133 arranged on the inner wall of the first housing 111 as well as a pipeline and a pump which are used for connecting the storage box 132 with the spraying member 133, the spraying member 133 and the cavity of the first test chambers 11 in each layer are both provided with corresponding spraying pipes, and a soil humidity sensor is arranged on the inner wall of the first housing 111; by using the liquid supply component, the maximum water content of the soil inside the first test chamber 11 is always maintained to 60%, or the deionized water can be continuously injected into the buffer cavities 134 by utilizing the liquid supply component, the pollutants carried in the pretreated solid soil in the first toxicity test are imported into the subsequent second test chambers 21 through the pipeline and pump connected with the buffer cavities 134;

as shown in FIG. 5, the liquid infiltration component includes 6 buffer cavities 134 correspondingly installed at the bottom of the first housing 111 one by one and communicated with the first test chambers 11, and an intercepting filter screen 135 arranged at a communication position between the buffer cavity 134 and the first housing 111, the buffer cavities 134 are connected with a water tank 136 through the pipeline and the pump, and the water tank 136 is arranged at a gap between the first test device 1 and the second test device 2 and fixedly connected with the outer side wall of the first test device 1; the use of the intercepting filter screen 135 can effectively avoid that the pretreated solid waste soil in the first test chambers 11 flow into the buffer cavities 134, arrangement of buffer cavities 134 can effectively prevent the block of the pipeline of the first connection component 131, and when in actual use, the first connection component 131 is used to connect the position of the buffer cavity 134 close to the upper part, the second test device 2 includes:

as shown in FIG. 2, 6 second test chambers 21 with the same structure and arranged in parallel, wherein the 6 second test chambers 21 are respectively connected with branch pipes on the pipeline of the first connection component 131, and a second monitoring device 22 erected above the second test chambers 21 and an auxiliary device 23;

as shown in FIG. 2, the auxiliary device 23 includes an air pump for supplying oxygen to the second test chambers 21 and a heating device for helping to heat the second test chambers 21, the air pump is connected with an air pipe 231 arranged in each second test chamber 21, and the heating device is connected with a heating plate 232 arranged in each second test chamber 21, specifically, the heating device is a commercially available electric heater and is communicated with the heating plate 232 through the heat-conducting pipe, and heat transfer is conducted by heating distilled water and other heat-conducting media; by utilizing the air pump and the heating device, a more suitable environment can be provided for cultivation of zebrafish, and the death of zebrafish caused by oxygen deficit, low temperature, high temperature and the like can be effectively avoided, thereby reducing the influence of these interference factors on accuracy rate of actual diagnosis;

the third test device 3 includes:

as shown in FIGS. 1 and 2, 6 third test chambers 31 with the same structure and arranged in parallel, and a second connection component 32 correspondingly connected with the 6 third test chambers 31 and the 6 second test chambers 21 one by one, wherein the second connection component 32 includes a pipeline and a pump.

Example 3

Figure 4:
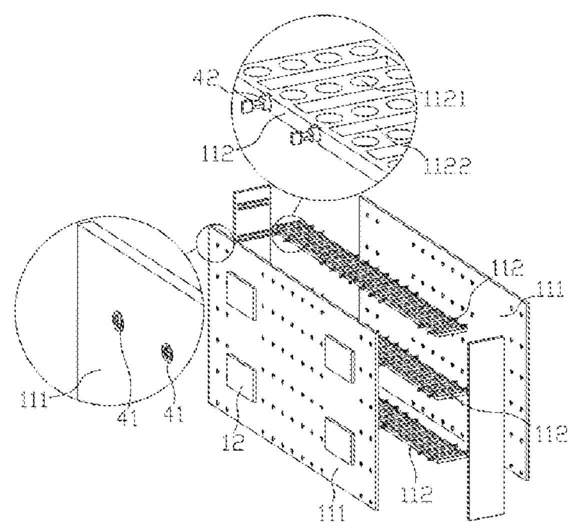
FIG. 4 is an exploded view of a first test device according to the disclosure.
Figure 7:
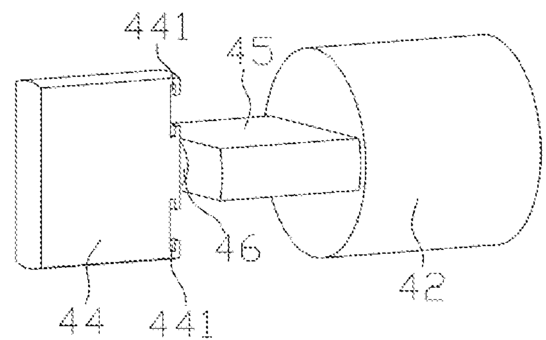
FIG. 7 is a structural diagram of an abutment rod of an abutment component according to the disclosure.

This example is basically the same as example 2, and the difference is that as shown in FIG. 4, the abutment component 4 includes:

as shown in FIGS. 4 and 6, an abutment sleeve 41 arranged on the clamping hole of the first housing 111, wherein a slidable transmission sleeve 43 is arranged in the abutment sleeve 41, and the transmission sleeve 43 is provided with a guide block 431 clamped with an arc groove 411 arranged on the inner side wall of the abutment sleeve 41, and as shown in FIGS. 4 and 7, an abutment rod 42 arranged on the embedded clapboard 112, wherein one side of the abutment rod 42 close to the abutment sleeve 41 is provided with a vertical plate-shaped first clamp head 44, the first clamp head 44 is connected with the abutment rod 42 through a horizontally arranged transverse plate-shaped second clamp head 45, and the second clamp head 45 is rotatably connected with the first clamp head 44 through a torsion spring 46, and the second clamping head 45 is fixedly connected with the abutment rod 42;

as shown in FIG. 6, the side surface of the abutment sleeve 41 is provided with a linear strip-shaped hole 412 corresponding to the horizontally arranged second clamp head 45, the abutment sleeves 41 on the upper and lower sides of the strip-shaped hole 412 are respectively provided with a clamp seat 413, and the clamp seat 413 is clamped with a clamp slot 441 matched with the first clamp head 44, the transmission sleeve 43 is provided with through holes 432 matched with the first clamp head 44 and the second clamp head 45, and the lengths of the through holes 432, the length of the first clamp head 44 and the length of the second clamp head 45 are equal, the inner side surfaces of the transmission sleeve 43 and the abutment sleeve 41 are provided with magnetic sheets whose magnetic poles are mutually repellent;

Through the arrangement of the above abutment component 4, the quick plug-in installation of the embedded clapboard 112 and the first housing 111 can be realized, so as to improve the installation efficiency of the first test chambers 11, and the quantity of the first test chambers 11 is rapidly adjusted according to demand on the practical diagnosis method.

Figure 8:
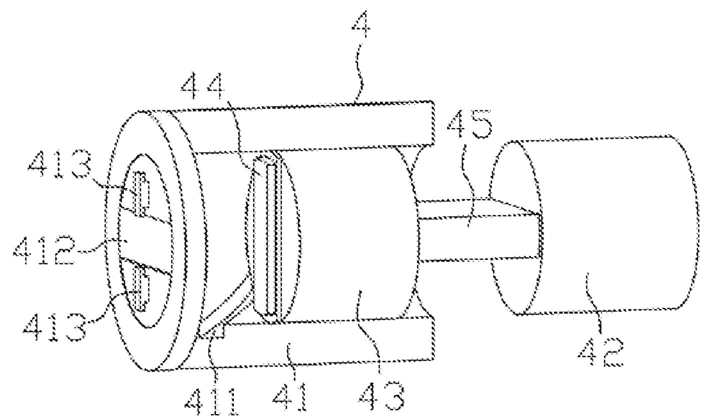
FIG. 8 is a diagram showing an abutment sleeve and an abutment rod of an abutment component are in an unclamping state according to the disclosure.
Figure 9:
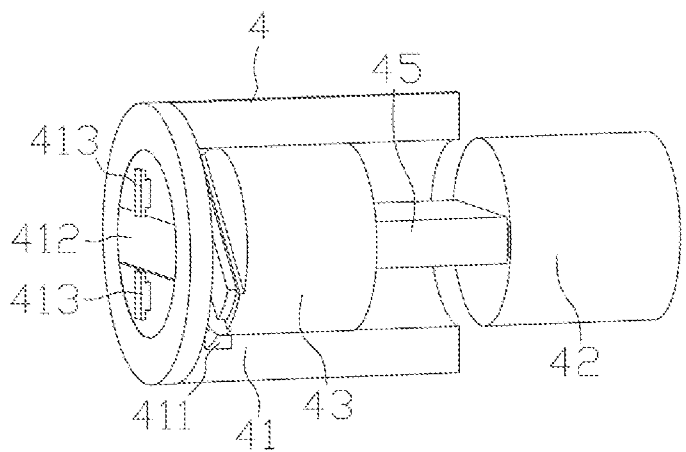
FIG. 9 is a diagram showing an abutment sleeve and an abutment rod of an abutment component are in a plug-in state according to the disclosure.
Figure 10:
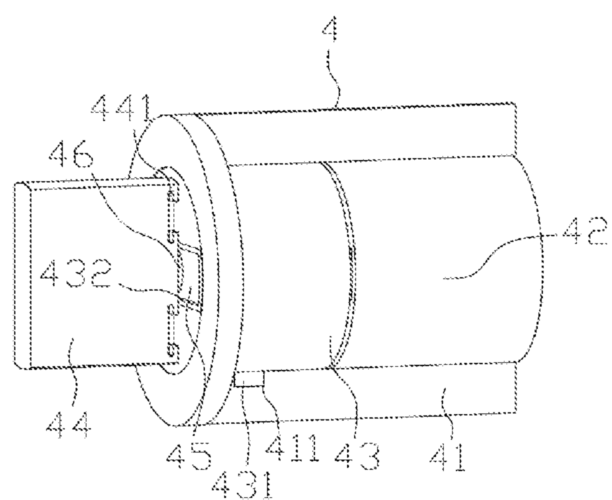
FIG. 10 is a diagram showing an abutment sleeve and an abutment rod of an abutment component are in a clamping state according to the disclosure.

The working method of the above abutment component 4 is as follows:

When the abutment rod 42 is not inserted or clamped, as shown in FIG. 8, the first clamp head 44 is maintained in a vertical direction and the second clamp head 45 is maintained in a horizontal direction, that is, the first clamp head 44 and the second clamp head 45 are crossed, when the abutment rod 42 is not inserted or clamped, as shown in FIG. 8, the transmission sleeve 43 in the abutment sleeve 41 is located at the initial position in the vertical direction of the through hole 432 under the action of a magnetic repulsion force, when the abutment rod 42 is inserted into the abutment sleeve 41, a state as shown in FIG. 8 is changed to a state as shown in FIG. 9, the first clamp head 44 is inserted into the through hole 432, and continuously pushes the transmission sleeve 43 to inward move against the magnetic repulsion force through the second clamp head 45. At the same time, under the action of the guide block 431 and the arc groove 411, the transmission sleeve 43 rotates in the process of inward moving, at this moment, the first clamp head 44 rotates with the transmission sleeve 43 against the torque of the torsion spring 46, when the through hole 432 of the transmission sleeve 43 rotates from a vertical direction to a horizontal direction, as shown in FIG. 10, with the continuous insertion of the abutment rod 42, the second clamp head 45 is inserted into the through hole 432 and allows the first clamp head 44 to pass through the strip-shaped hole 412. After the first clamp head 44 completely passes through the strip-shaped hole 412, the first clamp head 44 resets under the action of the torsion spring 46, and meanwhile the clamp groove 441 of the first clamp head 44 is clamped with the clamp seat 413 so as to realize the clamping between the abutment rod 42 and the abutment sleeve 41, when it is necessary to separate the abutment rod 42 from the transmission sleeve 43, the first clamp head 44 is rotated to be kept in the horizontal direction, the abutment rod 42 is pulled toward an opposite direction so that the abutment rod is separated from the transmission sleeve 43, and then the transmission sleeve 43 resets under the action of the magnetic repulsion force.

Example 4

The difference between this example and example 1 is that:

In the step 2, the impurities in the collected soil sample are removed, and the soil sample without the impurities are smashed and screened via a 10 mm sieve to obtain pretreated solid waste soil.

Example 5

The difference between this example and example 2 is that:

*Eisenia foetidas* which are subjected to intestinal cleaning treatment for 5 h in a humid environment are placed in the first test chamber 11 of the first test device 1;

Zebrafish which are subjected to fasting for 48 hours are placed in the second test chamber 21 of the second test device 2.

Example 6

The difference between this example and example 3 is that:

The first test device 1 includes 5 first test chambers 11 with the same structure and arranged in parallel at equal intervals in the first test chamber 11 of the first test device 1, the first connection device 13 includes a liquid supply component which was in one-to-one correspondence to 5 first test chambers 11 and used for supplying liquid to the first test chambers 11, the liquid infiltration component includes 5 buffer cavities 134 correspondingly installed at the bottom of the first housing 111 one by one and communicated with the first test chambers 11, the second test device 2 includes 5 second test chambers 21 with the same structure and arranged in parallel.

Example 7

The difference between this example and example 3 is that:

The first test device 1 includes 8 first test chambers 11 with the same structure and arranged in parallel at equal intervals in the first test chambers 11 of the first test device 1, the first connection device 13 includes a liquid supply component corresponding to eight first test chambers 11 one by one and used for supplying liquid to the first test chambers 11, the liquid infiltration component includes 8 buffer cavities 134 correspondingly installed at the bottom of the first housing 111 one by one and communicated with the first test chambers 11, the second test device 2 includes 8 second test chambers 21 with the same structure and arranged in parallel.

Application Example

By taking examples 1 and 2 as examples, a diagnosis method of ecotoxicity of solid waste soil in a pesticide production site includes the following steps:

step 1: collection of solid waste soil in a site multi-point distributed collection was performed on to-be-to diagnosed solid waste soil in a pesticide production site in combination with a layout principle of survey spots in the pesticide production site, soils in different collection sites were separately and independently stored at 5° C. and labeled to obtain a soil sample;

step 2: pretreatment of solid waste soil the impurities in the collected soil sample were removed, the soil sampled without the impurities were smashed, and screened via a 5-10 mm sieve to obtain pretreated solid waste soil; and step 3: diagnosis of ecotoxicity the pretreated solid waste soils in different collection sites were labeled in 5 groups for one experiment batch to labeled solid waste soils in group A1, group A2, group A3, group A4 and group A5; then the labeled solid waste soils were mixed with normal soils in 4 ratios to obtain 4 different experiment soils; wherein the solid waste soils labeled in this example were mixed with normal soils respectively in a mass ratio of 1:1, 1:2, 1:3 and 1:4 to obtain test soils;

Group A1: a11, A12, A13, A14,

Group A2: A21, A22, A23, A24,

Group A3: A31, A32, A33, A34,

Group A4: A41, A42, A43, A44,

Group A5: A51, A52, A53 and A54

Then the solid waste soil in group A1, group A2, group A3, group A4 and group A5 was put into 5 different first test chambers 11 respectively, the normal soil was recorded as group A6 and put into the sixth first test chamber 11, and each soil in each group was placed in different cavity layers of the first test chamber 11; the specific operations were as follows: A11 parts of experimental soil were placed into the bottom layer of the first test chamber 11 until A11 parts of experimental soil were located at the height of the first embedded clapboard 112, then the pretreated earthworm was put, then wheat seeds were put in the embedded hole 1121, and then the embedded clapboard 112 was inserted into the first housing 111; then the above steps were repeated successively, and A12 parts of test soil, A13 parts of test soil and A14 parts of test soil were loaded into the first test chamber 11 from bottom to upper layer; the steps were repeated to put the test soil in group A1, A2, A3, A4 and A5 and the normal soil in group A6 into the first test chambers 11;

then, zebrafish and deionized water were put into the second test chambers 21; wherein, 20 zebrafish were placed in each second test chamber 21;

hydroponic vegetables and deionized water were placed inside the third test chamber 31; wherein, the hydroponic vegetables were lettuce seedlings growing for day 10;

Initiate an experiment: the spraying member 133 was used to always maintain the maximum water content of the test soil inside the first test chambers 11 to be 60%; water containing pollutants, permeable from the first test chambers 11 and temporarily stored in the buffer cavities 134 was introduced into the second test chamber 21 by utilizing the first connection component 131;

the second connection component 32 was used to always maintain the one-to-one correspondence circulation of water currents in the second test chambers 21 and the third test chambers 31.

What is claimed is:

1. A method for diagnosing ecotoxicity of solid waste soil in an insecticide and pesticide production field is characterized by comprising the following steps of:

step one: collection of field solid waste soil by carrying out multi-point collection on solid waste soil of the insecticide and pesticide production field to be diagnosed by combining with an investigation point distribution principle of the insecticide and pesticide production field;

step two: pretreatment of solid waste soil by removing impurities from the collected soil, crushing, and sieving b rising a 5-10 mm sieve to obtain pretreated solid waste soil;

step three: diagnosis of ecotoxicity by synchronously carrying out a first toxicity test, a second toxicity test and a third toxicity test on the pretreated solid waste soil by using a diagnosis device; wherein the first toxicity test is an earthworm toxicity test and a plant germination toxicity test, the second toxicity test is a fish feeding toxicity test, and the third toxicity test is a plant root system extending toxicity test;

wherein the diagnostic device comprises a first test device (1) for performing the first toxicity test, a second test device (2) for performing the second toxicity test, and a third test device (3) for r performing the third toxicity test; the first test: device (1), the second test device (2) and the third test device (3) are connected in sequence;

wherein the first test device (1) comprises 5-8 first test cavities (11) which are identical in structure and are arranged in parallel at intervals, first monitoring devices (12) arranged in the intervals of the first test cavities (11), and a first connecting device (13) used for connecting the first test cavities (11) with the second test devices (2);

wherein each of the first test cavities (11) comprises a first shell (111) and 3-5 embedding partition plates (112) which are clamped in the first shell (11) from top to bottom in sequence; the first shell (111) adopts a transparent acrylic plate; the embedding partition plate (112) comprises partition plates (1121), embedding holes (1122) which are uniformly arranged on the partition plates (1121) and used for embedding seeds, and perforation slots through which earthworms can pass;

wherein the number of the first monitoring devices (12) is multiple, and the multiple first monitoring devices (12) are uniformly arranged in intervals of the first test cavities (11);

wherein the first connecting device (13) comprises a plurality of liquid supply devices for respectively supplying liquid to the 5-8 first test cavities (11), a liquid infiltration device arranged at the lower end of each first test cavity (11), and the first connecting device with one end connected with the liquid infiltration device;

wherein the second test device (2) comprises 5-8 second te (21) which are identical in structure and are arranged in parallel, second monitoring devices (22) arranged in the second test cavities (21), and an auxiliary device (23) erected above the second test cavities (21);

wherein the 5-8 second test cavities (21) are respectively connected with the other end of the first correcting device;

wherein the third test device (3) comprises 5-8 third test cavities (31) which are identical in structure and are arranged in parallel, and a second connecting device which is used for connecting the 5-8 third test cavities (31) and the 5-8 second test cavities (21) in a one-to-one correspondence mode.

2. The method as claimed in claim 1, wherein each of the liquid supply devices comprises a spraying device arranged on the inner wall of the first shell (111), and a pipeline and a connecting pump for connecting a storage tank for storing deionized water and the spraying device; and a soil humidity sensor is arranged inside the first shell (111).

3. The method as claimed in claim 1, wherein the liquid infiltration device comprises 5 to 8 buffer chambers which are installed at the bottom of the first casing (111) in a one-to-one correspondence and are communicated with the first casing (111), and an intercepting screen which is arranged at the communication position of the buffer chambers and the first casing (111).

4. The method as claimed in claim 1, wherein the auxiliary device (23) comprises an air pump for supplying oxygen to the second test chamber (21), and a heating device for the auxiliary heating of the second test chamber (21).

5. The method as claimed in claim 1, comprising pretreating the earthworms before placing the earthworms inside the first casing (111), the step of pretreating comprising putting the earthworms in a humid environment for gut purging far 3-5 hours.

6. The method as claimed in claim 1, comprising pretreating a zebrafish, then placing the zebrafish inside the second test chamber (21), the step of pretreating comprising stopping feeding for 35-48 h.

7. The method as claimed in claim 1, wherein a hydroponic vegetable is placed inside the third test chamber (31).

* * * * *